United States Patent [19]
Park et al.

[11] Patent Number: 5,232,842
[45] Date of Patent: Aug. 3, 1993

[54] METHOD FOR PREPARING CHITOSAN

[75] Inventors: Okmi Park, Tokyo; Hiroshi Miyoshi, Kanagawa; Jun Watanabe, Kanagawa; Tohru Chiba, Kanagawa; Isao Endo, Tokyo, all of Japan

[73] Assignees: Shin-Estu Chemical Co., Ltd., Tokyo; The Institute of Physical and Chemical Research, Saitama, both of Japan

[21] Appl. No.: 942,430

[22] Filed: Sep. 9, 1992

[30] Foreign Application Priority Data

Sep. 11, 1991 [JP] Japan .................................. 3-231893
Aug. 5, 1992 [JP] Japan .................................. 4-209203

[51] Int. Cl.$^5$ ......................... C12P 19/04; C12R 1/65
[52] U.S. Cl. ................................. 435/101; 435/171; 435/912; 536/20
[58] Field of Search ............... 435/171, 912, 101, 931; 536/20

[56] References Cited

U.S. PATENT DOCUMENTS

| | | | |
|---|---|---|---|
| 4,806,474 | 2/1989 | Hershberger | 435/101 |
| 4,970,150 | 11/1990 | Yaku et al. | 435/101 |
| 4,992,180 | 2/1991 | Onodera | 210/688 |
| 5,130,243 | 7/1992 | Kimura et al. | 435/95 |

OTHER PUBLICATIONS

JO2-215393 (Aug. 28, 1990) Shimomura et al. "Production of Chitosan Hydrolysate".

*Primary Examiner*—Herbert J. Lilling
*Attorney, Agent, or Firm*—McAulay Fisher Nissen Goldberg & Kiel

[57] ABSTRACT

According to the method for preparing chitosan of the present invention, chitosan is prepared by inoculating a filamentous fungi belonging to the family Mucoraceae into a culture medium for pre-cultivation containing yeast extract, malt extract, peptone, glucose and magnesium sulfate to perform pre-cultivation and then inoculating the pre-culture into a culture medium for main-cultivation having a composition essentially identical to that of the medium for pre-cultivation to perform the main-cultivation. Particularly preferred filamentous fungi belonging to the family Mucoraceae is *Absidia coerulea*. According to the method for preparing chitosan through the cultivation of microorganisms, chitosan exhibiting uniform quality can efficiently be produced and the method does not adversely affect the circumferential environment.

7 Claims, No Drawings

METHOD FOR PREPARING CHITOSAN

BACKGROUND OF THE INVENTION

The present invention relates to a method for mass production of chitosan by cultivating microorganisms, in particular, those belonging to the family Mucoraceae.

Recently, chitosan has attracted special interest as a biomass which is second to cellulose in importance. Chitosan is expected to be used in various fields, for instance, highmolecular flocculants for waste water and porous beads for immobilizing enzymes and microorganisms and so on. Chitosan is present extensively in the natural world and, therefore, can be prepared through extraction from natural products and purification of the extract. Industrially, chitosan has been prepared by subjecting shells of crustaceans such as shrimps and/or crabs to decalcification and deproteination to isolate chitin and then deacetylating the resulting chitin with a hot concentrated alkali solution.

However, this method requires the use of natural resources such as shrimps and/or crabs whose amount acceptable greatly varies depending on years and seasons and it is likewise apprehended that the natural resources are exhausted. Furthermore, the quality of the resources varies depending on the harvest-time. For this reason, it is difficult to stably supply the ingredients having fixed quality. If the ingredients are stored over a long time period to eliminate such disadvantage, they rot and give out a bad smell during storage, and it makes molecular weight decrease. Furthermore, the waste water discharged during the processes such as deacetylation of chitin is alkaline which has a high level of the biological oxygen demand (BOD) and becomes a cause of environmental pollution.

SUMMARY OF THE INVENTION

Accordingly, an object of the present invention is generally to solve the foregoing problems associated with the conventional methods for preparing chitosan and more specifically to provide a method for preparing chitosan through cultivation of microorganisms which permits effective production of chitosan having uniform quality and does not adversely affect the circumferential environment.

The inventors of this invention have investigated the conventional processes for industrially preparing chitosan which suffer from the foregoing problems and have taken note of the fact that a significant amount of chitosan is present in the cell wall of filamentous fungi belonging to the family Mucoraceae in addition to chitin. This fact is disclosed in Bartnicki-Garcia, S., Ann. Rev. Microbiol., 1968, 22, p. 87. The inventors have presumed that chitosan would be prepared if this filamentous fungi can be cultivated in a large scale. The inventors have conducted various studies based on this presumption and thus have completed the present invention.

According to the present invention, there is provided a method for preparing chitosan which comprises the steps of inoculating a filamentous fungi belonging to the family Mucoraceae into a culture medium for pre-cultivation containing yeast extract, malt extract, peptone, glucose and magnesium sulfate to perform pre-cultivation and then inoculating the resulting pre-culture into a culture medium for main-cultivation having a composition essentially identical to that of the medium for pre-cultivation to perform the main-cultivation.

DETAILED DESCRIPTION OF THE INVENTION

The method for preparing chitosan according to the present invention comprises inoculating a filamentous fungi belonging to the family Mucoraceae into a culture medium for pre-cultivation to perform pre-cultivation and then inoculating the resulting pre-culture into a culture medium for main-cultivation having a composition essentially identical to that of the medium for pre-cultivation to perform the main-cultivation.

The culture media for pre-cultivation and main-cultivation comprise 0.1 to 2.5 w/v % of yeast extract, 0.1 to 2.5 w/v % of malt extract, 0.5 to 8 w/v % of peptone, 1 to 10 w/v % of glucose and 0.1 to 1.4 w/v % of magnesium sulfate ($MgSO_4.7H_2$), preferably 0.3 to 2.1 w/v % of yeast extract, 0.3 to 2.1 w/v % of malt extract, 1.5 to 5 w/v % of peptone, 3 to 7 w/v % of glucose and 0.6 to 1.4 w/v % of magnesium sulfate ($MgSO_4.7H_2O$) and more preferably 1.2 to 1.8 w/v % of yeast extract, 1.2 to 1.8 w/v % of malt extract, 2.0 to 3.0 w/v % of peptone, 4 to 6 w/v % of glucose and 0.8 to 1.2 w/v % of magnesium sulfate ($MgSO_4.7H_2O$).

Among filamentous fungi belonging to the family Mucoraceae, preferred is *Absidia coerulea*. This strain has been preserved by Juridical Foundation: Institute of Fermentation (Domicile: 17-85, Juso-honmachi 2-chome, Yodogawa-ku, Osaka-shi, Japan) under an accession number of IFO 5301 and is available from Institute of Fermentation. The concentration of spores of the filamentous fungi to be inoculated into the culture medium for pre-cultivation suitably ranges from $10^5$ to $10^8$/100 ml.

The content of each component present in the culture medium for main-cultivation is preferably 1 to 7 times that of the medium for pre-cultivation. The content of chitosan in dry mycelia can increased by adjusting the concentrations of every components in the medium for main-cultivation to levels higher than those for the medium for pre-cultivation. The chitosan content in dry mycelia would be increased because the concentrations of nitrogen-containing components as the substrates in the medium, i.e., peptone and yeast extract having high nitrogen contents and the concentration of magnesium are high as compared with those for the medium for pre-cultivation. However, the use of these components in extremely high concentrations becomes a cause of substrate-inhibition and, therefore, any improvement in the chitosan content cannot be anticipated. For this reason, the concentration of each component of the medium for main-cultivation is preferably up to 7 times that for the pre-cultivation medium.

The pre-cultivation in the foregoing pre-cultivation medium is preferably carried out at a pH value on the order of 4 to 7 and more strictly ranging from 4.5 to 6.5. It is likewise preferred to carry out the main-cultivation in the main-cultivation medium at a pH value falling within the same range.

Optimum results can be obtained when the pre-cultivation and main-cultivation are carried out at a temperature ranging from 20 to 30 preferably ranging from about 23° to 28° C. and more preferably 24° to 27° C. for about 1 to 3 days.

Chitosan can be obtained from the main-culture medium by treating the culture with a hot sodium hydroxide solution, then extracting it with an aqueous acetic acid solution and making the extract alkaline. More specifically, an aqueous sodium hydroxide solution having a concentration ranging from 2 to 5 w/v % is added to dry mycelia obtained from the culture medium after the completion of the main-cultivation, followed by a heat-treatment performed at a temperature ranging from 100° to 125° C. for one hour, aqueous washing the residue and extraction with a acetic acid solution having a concentration ranging from 2 to 5 w/v %. Insolubles present in the resulting extract are removed through centrifugation and filtration and then an alkali such as sodium hydroxide is added to the resulting supernatant liquid to make the supernatant liquid weak alkaline to thus precipitate chitosan.

The cultivatings are not limited only to batch process but semi-batch process which is added limiting substrates such as Carbon source and Nitrogen source or a new culture medium, repetitive batch process, repetitive semi-batch process and continuous process are also applicable.

According to the method for preparing chitosan of the present invention, in which substances produced in an industrial scale are used as starting materials and which makes use of proliferation of microorganisms in a medium containing these industrially produced substances, chitosan having uniform quality can be efficiently prepared in accordance with a simple process within a short period of time. A stable supply of starting materials can ensured and the desired product having uniform quality can be obtained unlike the conventional methods for preparing chitosan in which natural resources are used as starting materials. Moreover, the method according to the present invention not include processes such as decalcification and deacetylation of chitin unlike the conventional methods and, therefore, the possibility of environmental pollution due to the discharge of waste water can be greatly reduced.

The present invention will hereinafter be described in more detail with reference to the following non-limitative working Examples.

EXAMPLE 1

A culture medium for pre-cultivation was prepared by mixing 3 g/l of yeast extract, 3 g/l of malt extract, 5 g/l of peptone, 10 g/l of glucose and 2 g/l of magnesium sulfate (heptahydrate). Spores ($4.5 \times 10^7$) of *Absidia coerulea* strain IFO 5301 were inoculated into 100 ml of the pre-cultivation medium contained in a 500 ml shaking flask. The flask was fitted to a rotary shaker and the spores were cultured at 27° and 200 rpm for 24 hours to give a pre-culture.

On the other hand, a culture medium for main-cultivation was separately prepared by admixing 3 g/l of yeast extract, 3 g/l of malt extract, 5 g/l of peptone, 10 g/l of glucose and 2 g/l of magnesium sulfate (heptahydrate) (having a composition identical to that for the pre-cultivation medium). The pre-culture obtained through the foregoing pre-cultivation (100 ml) was inoculated into 2 of the main-cultivation medium contained in a aeration-agitation fermenter and cultured at a temperature of 27° C., an air flow rate of 3 l/min and a number of revolution of 300 rpm for 70 hours.

The dry mycelia thus obtained through the main-cultivation were heat-treated at 121 for one hour in a 2 w/v % aqueous solution of sodium hydroxide. The mycelia thus heat-treated were extracted with a 2 w/v % acetic acid solution. Insolubles present in the resulting extract were removed through centrifugation and filtration and then sodium hydroxide was added to the resulting supernatant liquid to make the supernatant liquid weak alkaline to thus precipitate 1.6 g of chitosan. The precipitates were confirmed to be chitosan by IR spectroscopic analysis and nuclear magnetic resonance spectrometric measurement (NMR). The yield with respect to the dry mycelia charged wa found to be 8%.

EXAMPLE 2

A pre-culture was prepared under the same conditions used in Example 1.

On the other hand, a culture medium for main-cultivation was prepared by admixing 15 g/l of yeast extract, 15 g/l of malt extract, 25 g/l of peptone, 50 g/l of glucose and 10 g/l of magnesium sulfate (heptahydrate) (the mixing ratio of each component was the same as that for the pre-cultivation medium, but the concentration of each component was 5 times that used in the pre-cultivation medium). The pre-culture (100 ml) obtained above was inoculated into 2 l of the main-cultivation medium prepared above and contained in an aeration-agitation fermenter and cultured at a temperature of 27° C., an air flow rate of 3 l/min and a number of revolution of 300 rpm for 70 hours.

The dry mycelia thus obtained were subjected to a heat-treatment with a solution of caustic soda, extraction and precipitation performed under the same conditions used in Example 1 to give 15.2 g of chitosan. The yield with respect to the dry mycelia charged was found to be 23%.

EXAMPLE 3

A pre-culture was prepared under the same conditions used in Example 1.

On the other hand, a culture medium for main-cultivation was prepared by admixing 21 g/l of yeast extract, 21 g/l of malt extract, 35 g/l of peptone, 70 g/l of glucose and 14 g/( of magnesium sulfate (heptahydrate) (the mixing ratio of each component was identical to that used in the pre-cultivation medium, but the concentration of each component was 7 times that used in the precultivation medium). The main-cultivation was performed in the same manner used in Example 1 except that 100 ml of the pre-culture obtained above was used to give a main-culture.

The main-culture thus obtained was subjected to a heat-treatment with a solution of caustic soda, extraction and precipitation performed under the same conditions used in Example 1 to give 9.4 g of chitosan. The yield with respect to the dry mycelia charged was found to be 14%.

EXAMPLE 4

A pre-culture was prepared under the same conditions used in Example 1.

On the other hand, a of culture media for main-cultivation were prepared in the same manner used in Example 1 except that; in the first medium, 15 g/l, instead of 3 g/l, yeast extract was used; in the second medium, 15 g/l, instead of 3 g/l, malt extract was used; in the third medium, 25 g/l, instead of 5 g/l, peptone was used; in the fourth medium, 50 g/l, instead of 10 g/l, glucose was used; in the fifth medium, 10 g/l. instead of 2 g/l, magnesium sulfate (heptahydrate) was used. The pre-culture (5 ml each) obtained above was inoculated into the main-cultivation media (100 ml each) prepared above and contained in flasks and then cultured at a temperature of 27° C. and a number of revolution of 200 rpm for 72 hours. The main-culture thus obtained was subjected to a heat-treatment with a solution of caustic soda, extraction and precipitation performed under the same conditions used in Example 1 to give chitosan. The content of chitosan in each main-culture relative to that observed in Example 1 was 1.52 for the main-cultivation medium in which only the yeast extract content was increased; 1.40 for the main-cultivation medium in which only the peptone content was increased; or 1.66 for the main-cultivation medium in which only the magnesium sulfate (heptahydrate) content was increased, but any change in the chitosan content was not observed for the remaining main-cultivation media.

EXAMPLE 5

A pre-culture was prepared under the same conditions used in Example 1.

On the other hand, a number of culture media for main-cultivation were prepared in the same manner used in Example 1 except that; in the first medium, 21 g/l, instead of 3 g/l, yeast extract was used; in the second medium, 21 g/l, instead of 3 g/l, malt extract was used; in the third medium, 35 g/l, instead of 5 g/l, peptone was used; in the fourth medium, 70 g/l, instead of 10 g/l, glucose was used; in the fifth medium, 14 g/l, instead of 2 g/l, magnesium sulfate (heptahydrate) was used. The pre-culture (5 ml each) obtained above was inoculated into the main-cultivation media (100 ml each) prepared above and contained in flasks and then cultured at a temperature of 27° C. and a number of revolution of 200 rpm for 72 hours. The main-culture thus obtained was subjected to a heat-treatment with a solution of caustic soda, extraction and precipitation performed under the same conditions used in Example 1 to give chitosan. The content of chitosan in each main-culture relative to that observed in Example 1 was 1.29 for the main-cultivation medium in which only the yeast extract content was increased; 0.76 for the main-cultivation medium in which only the peptone content was increased; or 1.75 for the main-cultivation medium in which only the magnesium sulfate (heptahydrate) content was increased, but only a slight change in the chitosan content was observed on the remaining main-cultivation media.

What is claimed is:

1. A method for preparing chitosan comprising:
   a) subjecting a filamentous fungi belonging to the family Mucoraceae to culture conditions in a medium containing yeast extract, malt extract, peptone, glucose and magnesium sulfate to prepare a preculture; and
   b) subjecting the preculture to main cultivation conditions in a medium containing yeast extract, malt extract, peptone, glucose and magnesium sulfate to prepare a main culture.

2. The method of claim 1 which further comprises treating the main culture with a hot caustic soda solution, extracting the thus treated culture with an aqueous solution of acetic acid and making the extract obtained alkaline to isolate and precipitate chitosan.

3. The method of claim 1 wherein the filamentous fungi is Absidia coerulea.

4. The method of claim 1 wherein the concentration of each component of the medium in step b) is 1 to 7 times that of the corresponding component of the medium of step a).

5. The method of claim 1 wherein the pH value of the media for steps a) and b) ranges from 4 to 7.

6. The method of claim 1 wherein steps a) and b) are carried out a temperature ranging from 20° to 30° C.

7. The method of claim 1 wherein an aqueous sodium hydroxide solution having a concentration ranging from 2 to 5 w/v % is admixed with the main culture, the admixture is heated for one hour at 100°–125° C., and then extracted with acetic acid having a concentration from 2 to 5 w/v % to produce an extract, and the extract is mixed with an alkali to precipitate chitosan.

* * * * *